United States Patent [19]
Arick et al.

[11] Patent Number: 5,419,762
[45] Date of Patent: May 30, 1995

[54] APPARATUS AND METHOD FOR EQUALIZING THE PRESSURE IN THE MIDDLE EAR

[76] Inventors: Daniel Arick, 20 W. 64th St., Apt. 17D, New York, N.Y. 10023; Shlomo Silman, 3030 Emmons Ave., Apt. 3R, Brooklyn, N.Y. 11235

[21] Appl. No.: 166,314

[22] Filed: Dec. 10, 1993

Related U.S. Application Data

[63] Continuation-in-part of Ser. No. 109,173, Aug. 19, 1993, abandoned.

[51] Int. Cl.[6] ............................................. A61M 37/00
[52] U.S. Cl. ......................................................... 604/26
[58] Field of Search .................... 604/23, 26, 275, 54, 604/94; 128/200.12, 200.22, 204.21, 205.18, 205.24, 207.18

[56] References Cited

U.S. PATENT DOCUMENTS

| | | | |
|---|---|---|---|
| 474,035 | 5/1892 | Vant Woud | 128/200.22 |
| 514,448 | 2/1894 | DeSant | 128/205.18 |
| 728,526 | 5/1903 | Wantz | 604/26 |
| 1,020,647 | 3/1912 | Holland et al. | 128/200.22 |
| 1,120,673 | 12/1914 | Bayer | 128/205.18 |
| 4,660,555 | 4/1987 | Payton | 128/207.18 |
| 4,782,832 | 11/1988 | Trimble et al. | 128/207.18 |

FOREIGN PATENT DOCUMENTS 0818186  6/1937  France .................. 128/205.18

Primary Examiner—C. Fred Rosenbaum
Assistant Examiner—Frank Wilkens, III
Attorney, Agent, or Firm—McAulay Fisher Nissen Goldberg & Kiel

[57] ABSTRACT

An apparatus for equalizing pressure in a middle ear including a compressor, activating means coupled to the compressor, the activating means having a closed state and an open state, the open state providing a continuous flow of air from the compressor at a predetermined pressure, and a tapered nostril plug in communication with the compressor, the nostril plug having a distal opening for delivering the continuous flow of air, the predetermined pressure being in the range of approximately 0.5 p.s.i. to approximately 3.0 p.s.i. In addition, an apparatus for equalizing pressure in a middle ear including a compressor, activating means coupled to the compressor, the activating means having a closed state and an open state, the open state providing a continuous flow of air from the compressor at a predetermined rate; and a tapered nostril plug in communication with the compressor, the nostril plug having a distal opening for delivering the continuous flow of air, the predetermined rate being in the range from approximately 1.0 liter/minute to approximately 4.0 liters/minute.

4 Claims, 3 Drawing Sheets

APPARATUS AND METHOD FOR EQUALIZING THE PRESSURE IN THE MIDDLE EAR

RELATED APPLICATION

This application is a continuation-in-part of application Ser. No. 08/109,173, filed Aug. 19, 1993 now abandoned.

BACKGROUND OF THE INVENTION

The present invention is related to an apparatus for equalizing the pressure in the middle ear. More specifically, the present invention relates to a portable, pocket-size apparatus which may be used to equalize the pressure in the middle ear.

An imbalance between the pressure in the middle ear and the ambient pressure can result in the sensation of ear clogging, generally referred to as Eustachian Tube Dysfunction (ETD). Patients often suffer from ETD as a result of a cold, allergies, or descent in an aircraft from high altitude. ETD, if not treated or naturally relieved, may lead to chronic traumatic inflammation of the middle ear, also known as aerotitis media, aviator's ear, otic barotrauma, barotitis media, and aviation otitis.

The middle ear cavity communicates with the pharynx via the Eustachian tube. The Eustachian tube is usually closed, however, it opens during swallowing and yawning. In order to equalize the pressure in the middle ear the Eustachian tube must be opened.

Sufferers of ETD and aerotitis media, have attempted to relieve any discomfort due to the affliction by yawning, swallowing, chewing gum, and closing the nostrils and blowing lightly to attempt to equalize the pressure in the middle ear. These methods, however, yield unpredictable results.

In extreme cases, fluid may build up behind the ear drum leading to complications including hearing loss. While some sufferers of ETD and aerotitis media have minimal discomfort which lasts merely during the descent or ascent in an airplane, others have more serious symptoms. In these cases, it is often necessary for a sufferer of aerotitis media to visit an Otolaryngologist who manually equalizes the middle ear pressure with the environment.

The Otolaryngologist normally employs one of two methods to equalize the pressure in the middle ear. The first method employed involves the use of steroids and/or antibiotics to alleviate any discomfort. An alternative method, known as the Politzer maneuver, requires the Otolaryngologist to use a tube to force air into the sufferer's nose. When the sufferer swallows, the Eustachian tube opens, and air is forced into the middle ear to equalize the middle ear pressure.

Accordingly, it is an objective of the present invention to provide an apparatus for performing the Politzer maneuver.

It is a further objective of this invention to provide a portable, compact apparatus which may be easily transported to alleviate any discomfort of an ETD or aerotitis media sufferer.

BRIEF DESCRIPTION

The present invention provides a relatively constant flow of air. The flow source is connected to a nostril plug through a channel. When the nostril plug is inserted into the sufferer's nose, air is supplied from the source into the nostril through the channel. Means for regulating the air flow supplied by the flow source is also provided.

The apparatus is operated by inserting the nostril plug into one nostril while closing the other nostril. The other nostril is closed by applying pressure to the outer side of the nostril and pushing it to seal the second nostril. The means for regulating air flow then permits a relatively continuous flow of air into the first nostril. The sufferer must then swallow to open the Eustachian tube to permit the air to enter the middle ear and equalize the middle ear pressure.

DETAILED DESCRIPTION OF THE INVENTION

Figure 1:
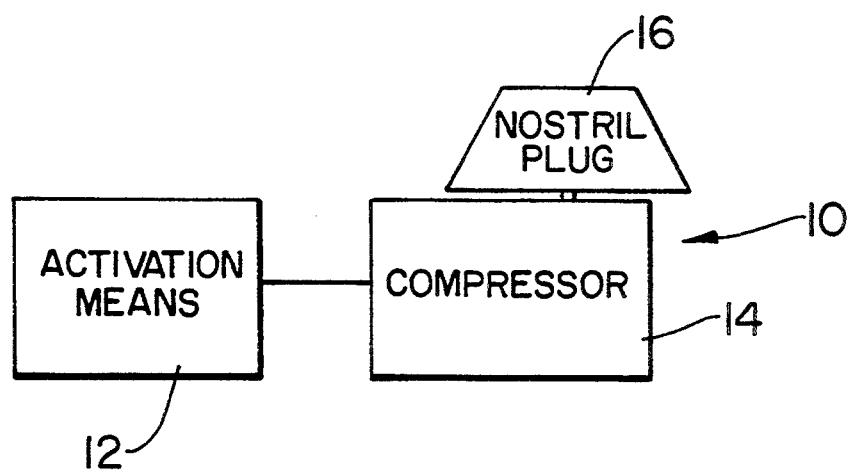
FIG. 1 is a block diagram illustrating the present invention.

Referring to FIG. 1, a presently preferred embodiment of pressure equalizing apparatus 10 according to the present invention includes activation means 12, compressor 14 and nostril plug 16.

Figure 2:
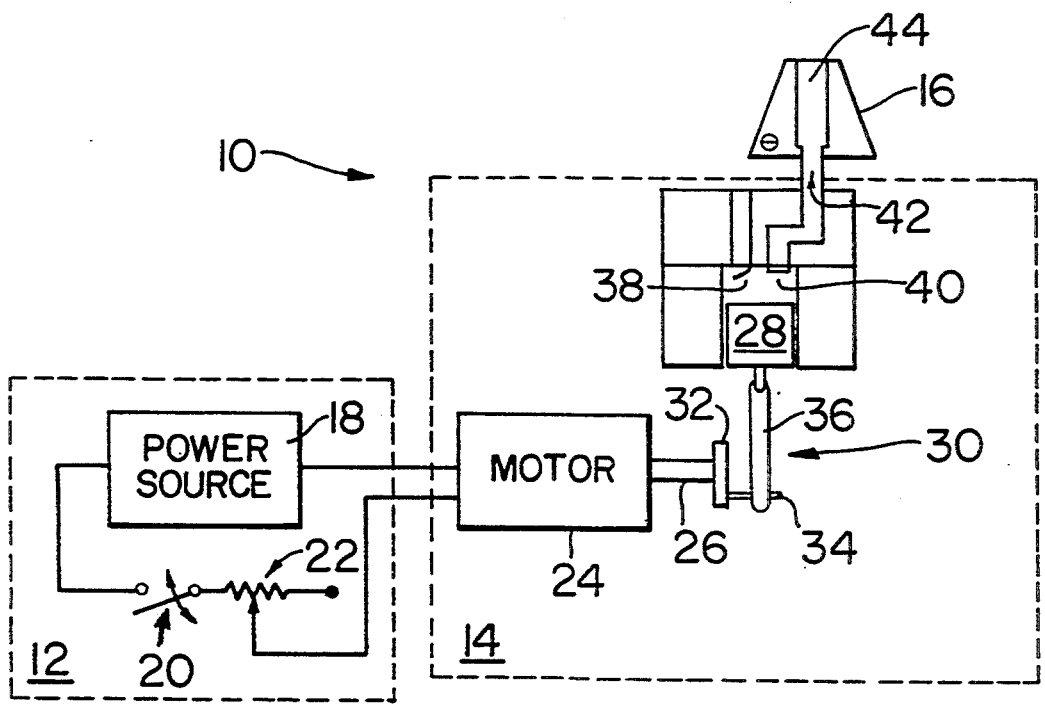
FIG. 2 is a schematic/cross-sectional view of a first embodiment of the present invention.

Referring to FIG. 2, activation means 12 includes power source 18, switch 20 and power variation means 22. Compressor 14 is activated by activation means 12. More specifically, compressor 14 includes motor 24 having motor shaft 26. Motor shaft 26 is connected to piston 28 through pivoting linkage 30. Pivoting linkage 30 includes rotating disk 32 having pin 34 extending transversely therefrom, and arm 36. Pin 34 pivotally engages arm 36. Arm 36 pivotally drives piston 28 upon rotary motion of shaft 26 and disk 32. Oscillation of piston 28 effects operation of flutter valves 38 and 40. Deflection of flutter valves 38 and 40 operate to create air flow through exit port 42. Exit port 42 communicates with channel 44 in nostril plug 16.

Figure 3:
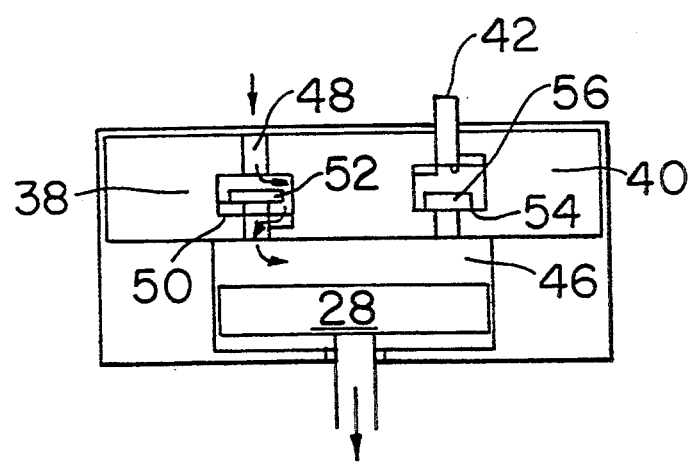
FIG. 3 is a cross-sectional view illustrating operation of the flutter valves during the downward stroke of the piston.

Referring to FIG. 3, during the downward stroke of piston 28, flutter valve 38 operates to allow air to be drawn into chamber 46 through port 48. More specifically, shoulder 50, having radially extending ridges and channels, prevents disk 52 from sealing off port 48 during the downward stroke of piston 28. Simultaneously, flutter valve 40 prevents the drawing of air through exit port 42. Shoulder 54 is relatively smooth, allowing disk 56 to provide a seal to prevent the drawing of air through exit port 42.

Figure 4:
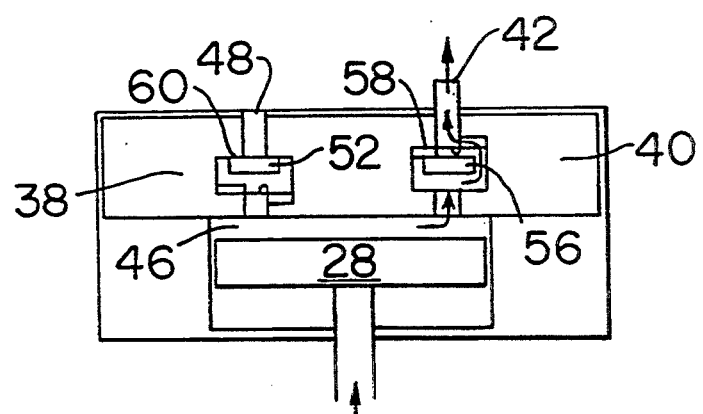
FIG. 4 is a cross-sectional view illustrating operation of the flutter valves during the upward stroke of the piston; and, FIG. 5 is a perspective view of a an alternate nostil plug for use with the present invention.

Referring to FIG. 4, during the upward stroke of piston 28, air which was previously drawn into chamber 46 during the downward stroke of piston 28, is expelled through exit port 42 by operation of flutter valve 40. During the upward stroke of piston 28, shoulder 58 and disk 56 operate similar to disk 52 and shoulder 50 during the downward stroke. Simultaneously, flutter valve 38 prevents the expulsion of air through port 48. During the upward stroke of piston 28, disk 52 and shoulder 60 operate similar to disk 56 and shoulder 54 during the downward stroke of piston 28.

Compressor 14 provides a rapid succession of pulses of air. The succession of pulses, however, is so rapid that a pressure gauge indicates an approximately constant air flow and air pressure at exit port 42. Accordingly, the term continuous flow will be used throughout to define the embodiments in which continuous air flow or a series of rapid air pulses create the air flow.

Switch 20 may include means to hold switch 20 in the on position. In an alternate embodiment, switch 20 may require pressure to maintain the on position. Additionally, power variation means 22 acts to vary the power supplied to motor 24, thereby varying the rotational speed of shaft 36 and thus, regulating air pressure supplied through exit port 42 and nostril plug channel 44. Power source 18 may include batteries.

Pressure equalizing apparatus 10 is operated by inserting nostril plug 16 into a first nostril. The operator creates a seal by inserting nostril plug 16 into the first nostril. The operator's second nostril is collapsed using a free hand to prevent leakage therethrough. Activation means 12 is used to control compressor 14. Accordingly, air is supplied through nostril plug 16 into the first nostril. The operator may then adjust the air pressure delivered to the first nostril by adjusting power variation means 22. The operator then swallows, opening the Eustachian tube to allow equalization of middle ear pressure with the ambient pressure.

Nostril plug 16 has a tapered shape to accommodate varying nostril sizes. Preferably, nostril plug 16 has an angle of inclination, Θ, of approximately 70°, a base diameter of approximately of 1.0 inch tapering to a tip diameter of approximately 0.375 inches. The diameter of channel 44 is preferably approximately 0.0938 inches.

The compressor embodiment of compressor 14 must generate sufficient air pressure at the exit of channel of 42 to operate effectively. The air pressure required ranges from approximately 0.5 pounds/inch$^2$ (p.s.i.) to approximately 3.0 p.s.i. Preferably, the air pressure is approximately 2.0 p.s.i. The flow rate of air should be within the range of 0.5 liter/minute to 4.0 liters/minute. Preferably, the flow rate should be between 1.5 liters/minute and 2.0 liters/minute.

Figure 5:
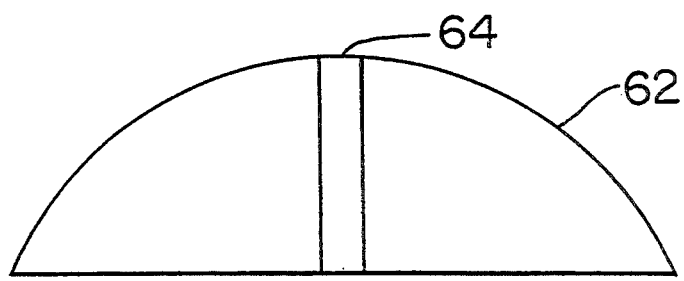

Referring to FIG. 5, an alternate embodiment of a nostril plug includes spherically tapered surface 62 and a channel 64 communicating therewith. Spherically tapered surface 62 effects a seal with a variety of nostril sizes.

In an alternate embodiment, an inhalable gas, stored in a container under pressure may be used in conjunction with a valve to provide a relatively constant flow of gas to a nostril plug.

In a further embodiment, a motorized fan may be used to replace the compressor to generate the necessary pressure or air flow.

While preferred embodiments of the present invention have been shown and described, it will be understood by those skilled in the art that various changes and modifications, could be made without varying from the scope of the present invention.

What is claimed is:

1. A method for equalizing pressure in a middle ear of a patient comprising the steps of:
    inserting a sealing nostril plug having a channel therethrough into a first nostril,
    sealing a second nostril,
    providing a continuous flow of air from a hand held air source through said channel into said first nostril, and
    causing the patient to swallow during said step of providing a continuous flow until pressure equalization is achieved.

2. The method of claim 1 wherein said continuous flow of air is substantially in the range from 0.5 liters per minute to 4.0 liters per minute.

3. The method of claim 1 wherein said flow of air is substantially in the range from 1.0 liters per minute to 2.5 liters per minute.

4. The method of claim 1 further comprising the steps of:
    adjusting the rate of said continuous flow and repeating said step of causing the patient to swallow.

* * * * *